(12) United States Patent
Park et al.

(10) Patent No.: US 11,224,554 B2
(45) Date of Patent: Jan. 18, 2022

(54) HEATING ASSEMBLY FOR MASSAGE CHAIR INCLUDING SEPARATE HEATING ELEMENT AND MASSAGE CHAIR COMPRISING THE SAME

(71) Applicant: Coway Co., Ltd., Chungcheongnam-do (KR)

(72) Inventors: Kyung Hwan Park, Seoul (KR); Chang Hee Han, Seoul (KR); Jin Won Park, Seoul (KR); Yeon Soo Seong, Seoul (KR); Byoung Chan Bae, Seoul (KR); Joong Keun An, Seoul (KR)

(73) Assignee: COWAY CO., LTD., Chungcheongnam-Do (KR)

( * ) Notice: Subject to any disclaimer, the term of this patent is extended or adjusted under 35 U.S.C. 154(b) by 268 days.

(21) Appl. No.: 16/476,425

(22) PCT Filed: Jan. 4, 2018

(86) PCT No.: PCT/KR2018/000177
§ 371 (c)(1),
(2) Date: Jul. 8, 2019

(87) PCT Pub. No.: WO2018/128415
PCT Pub. Date: Jul. 12, 2018

(65) Prior Publication Data
US 2019/0374425 A1    Dec. 12, 2019

(30) Foreign Application Priority Data

Jan. 6, 2017  (KR) .................. 10-2017-0002576
Apr. 7, 2017  (KR) .................. 10-2017-0045172

(51) Int. Cl.
*A61H 15/02*  (2006.01)
*A61H 15/00*  (2006.01)

(52) U.S. Cl.
CPC ......... *A61H 15/02* (2013.01); *A61H 15/0078* (2013.01); *A61H 2015/0042* (2013.01);
(Continued)

(58) Field of Classification Search
None
See application file for complete search history.

(56) References Cited

U.S. PATENT DOCUMENTS 5,460,598 A  * 10/1995  Yamasaki .......... A61H 15/0078
                                                    601/115
5,741,218 A  *  4/1998  Fujii ........................ A61H 1/00
                                                    601/90
(Continued)

FOREIGN PATENT DOCUMENTS

GN       103313691 A      9/2013
JP       2003038593 A     2/2003
(Continued)

OTHER PUBLICATIONS

International Search Report PCT/KR2018/000177, dated Apr. 16, 2018, 4 Pages.

*Primary Examiner* — Samchuan C Yao
*Assistant Examiner* — Savannah L Gabriel
(74) *Attorney, Agent, or Firm* — Brooks Kushman P.C.

(57) ABSTRACT

A heating assembly for a massage chair, wherein a heating element is separately operated. The heating assembly according to an embodiment having a first bracket with a plurality of massage balls rotatably mounted to the first bracket. A massage assembly is fixed to the first bracket and can perform at least one of up-and-down and left-and-right motions. A second bracket is mounted to the massage assembly or the first bracket A support part inserted at one end thereof into the second bracket. A heating element is mounted to the support part and an airbag is fixed to the support part so as to be opposite to the heating element.

(Continued)

Wherein the heating assembly is mounted inside the backrest of a massage chair.

9 Claims, 10 Drawing Sheets

(52) U.S. Cl.
CPC ............... *A61H 2201/0103* (2013.01); *A61H 2201/0149* (2013.01); *A61H 2201/0192* (2013.01); *A61H 2201/0207* (2013.01); *A61H 2201/0228* (2013.01); *A61H 2201/1642* (2013.01); *A61H 2201/1669* (2013.01)

(56) References Cited

U.S. PATENT DOCUMENTS

| | | | | |
|---|---|---|---|---|
| 2009/0036809 | A1* | 2/2009 | Nishio | A61H 15/0078 601/134 |
| 2009/0177128 | A1* | 7/2009 | Fukuyama | A61H 15/0078 601/98 |
| 2009/0270780 | A1* | 10/2009 | Wu | A61H 7/007 601/134 |
| 2010/0198120 | A1* | 8/2010 | Tago | A61H 1/0292 601/134 |
| 2012/0172768 | A1* | 7/2012 | Ikebe | A61F 7/00 601/19 |

FOREIGN PATENT DOCUMENTS

| | | |
|---|---|---|
| JP | 2012196408 A | 10/2012 |
| JP | 2013066509 A | 4/2013 |
| JP | 5437291 B2 | 3/2014 |
| KR | 200260012 Y1 | 1/2002 |
| KR | 1020020078516 A | 10/2002 |
| KR | 101013002 B1 | 2/2011 |
| KR | 1020130139585 A | 12/2013 |
| KR | 1020140070975 A | 6/2014 |
| KR | 1020140088748 A | 7/2014 |
| KR | 1020140137099 A | 12/2014 |
| KR | 101479521 B1 | 1/2015 |
| KR | 1020150067020 A | 6/2015 |
| KR | 1020150145927 A | 12/2015 |
| KR | 1020160125879 A | 11/2016 |
| KR | 1020170112910 A | 10/2017 |

\* cited by examiner

FIG. 8A
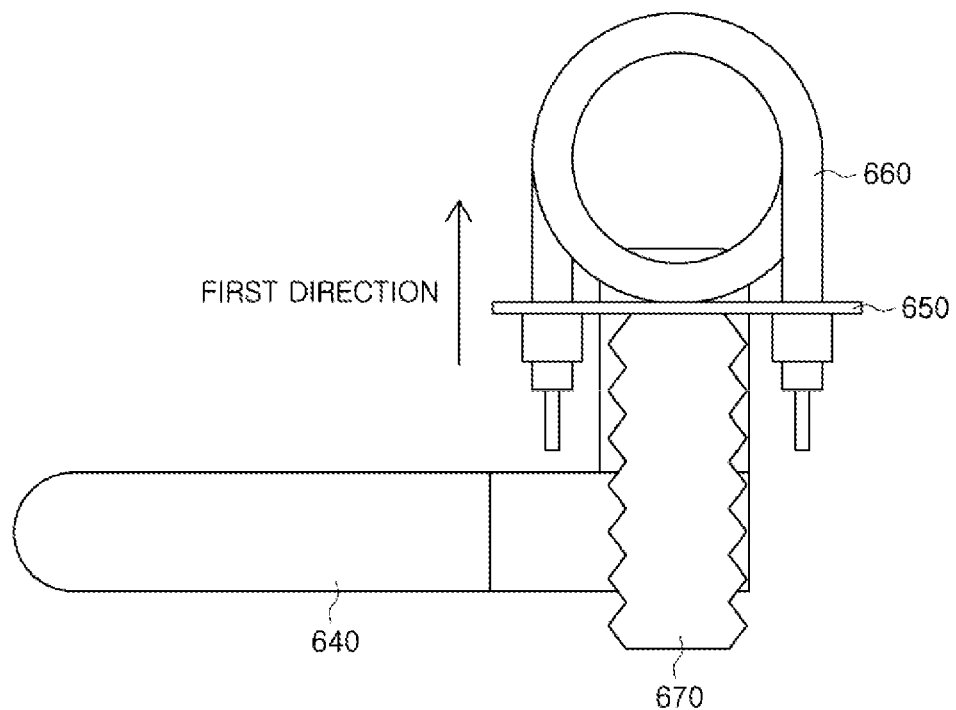
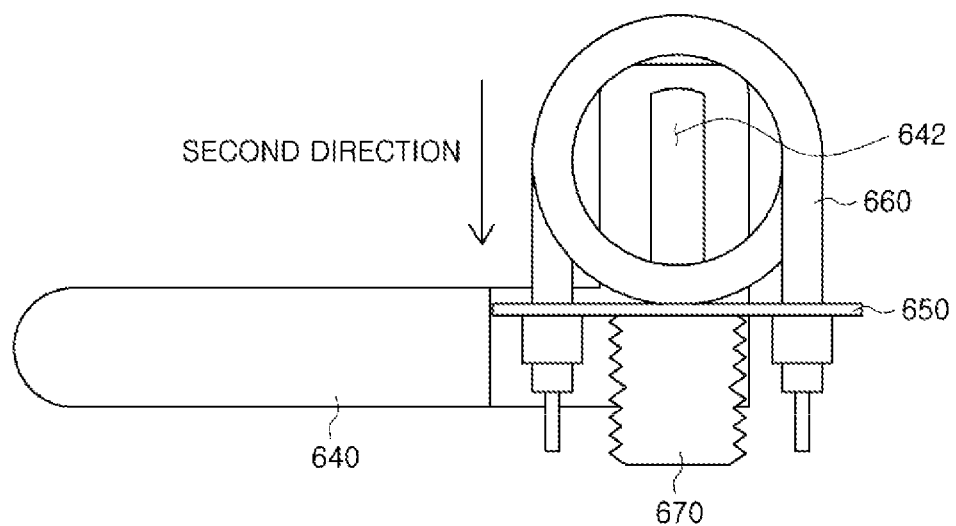
FIG. 8B

HEATING ASSEMBLY FOR MASSAGE CHAIR INCLUDING SEPARATE HEATING ELEMENT AND MASSAGE CHAIR COMPRISING THE SAME

CROSS-REFERENCE TO RELATED APPLICATION

This application is the U.S. national phase of PCT Application No. PCT/KR2018/000177 filed on Jan. 4, 2018, which claims priority to KR Patent Application No. 10-2017-0002576 filed on Jan. 6, 2017 and KR Patent Application No. 10-2017-0045172 filed on Apr. 7, 2017 the disclosures of which are incorporated in their entirety by reference herein.

TECHNICAL FIELD

The present invention relates to a heating assembly for use in a massage chair, and more specifically, to a heating assembly separately provided with a massage ball for performing a massage function and a heating element for performing a heating function, thus being able to provide a massaging feeling and a sense of warmth, and a massage chair including the same.

BACKGROUND ART

Many people get massages to relieve the stiff body caused by stress, muscular knotting due to lack of exercise, and so on. However, since there are people who cannot get massages from professional massagers for various reasons, massage chairs for convenient use at homes have been developed and used.

Among various types of massage chairs, one type of massage chair has been developed, which has a warm ball assembly mounted inside a backrest such that warm balls massage the back muscles and give a sense of warmth as they move.

As the patent documents relating to the warm ball assembly, reference can be found in Korean Registered Patent No. 10-1479521, Japanese Patent Application Laid-Open No. 2013-066509, and Korean Patent Laid-Open Publication No. 2002-0078516, among others.

The warm ball assembly according to the related arts mentioned above commonly includes a bracket movable up and down, which supports warm balls and also transfers (through separate wires) the power for generating heat, and a plurality of warm balls provided in the bracket to heat up.

The warm ball includes an embedded heat wire or sheath heater and is heated by the power transferred from the power supply. In addition, since the warm ball is fixed to the bracket, it is moved together when the bracket is moved up and down or left and right, and at the same time, the warm ball fixed to the bracket is also rotated by itself to provide a massaging feeling.

That is, the warm balls heat up and are also moved vertically together with the bracket according to the up and down movement of the bracket. In this process, upon contacting the back or shoulder of the user, the warm ball is rotated by itself, thereby providing a massaging feeling and sense of warmth at the same time.

Such a related warm ball assembly has the following problems.

First, there is a problem associated with heating of the bracket. Since the bracket is directly connected to a shaft member of the warm ball to fix the warm ball, the bracket is also transferred with heat and heated as the warm ball is heated. However, while the warm ball is generally made of a soft material such as rubber to provide a massaging feeling, the bracket is generally made of a hard metal material in order to withstand the load such that, when the power is supplied to heat the warm ball, the bracket is heated to a higher temperature than the warm ball.

Indeed, in many massage chairs, the user feels the sense of warmth on the back due to the heat of the bracket rather than the heat of the warm ball which is in direct contact with the back of the user. Such a heating phenomenon of the bracket causes not only the problem of losses of heat and power through the bracket, but also the problem of deteriorating sense of warmth during massage and the problem of decreasing durability of the bracket due to repeated heating and cooling of the bracket made of metal material.

Second, in order to solve the above problem, the warm ball may be made of other materials such as ceramics with a higher heat transfer rate than the metal bracket, but the warm ball made of such materials causes noise during self-rotation. Considering that the warm ball assembly is generally mounted adjacent to the user's back or neck regions, the noise is an issue that cannot be overlooked.

Third, in order to heat the warm ball, eventually, it is necessary to supply power to the rotating warm ball, which makes the structure of the warm ball complicated, making it difficult to manufacture, and causing frequent failure. When the warm ball is broken, it needs to be replaced with a new warm ball, which causes the manufacturer an increased cost, as well as inconvenience of the user.

Fourth, there is a disadvantage that it is difficult to accurately provide a sense of warmth to a specific region where the user wants to feel the sense of warmth, since the sense of warmth felt by the user is due to the heat of the bracket rather than the heat of the warm ball which is in direct contact with the user.

(Patent Document 1) KR 10-1479521B1
(Patent Document 2) JP 2013-066509A
(Patent Document 3) KR 2002-0078516A
(Patent Document 4) JP 2003-038593A2
(Patent Document 5) KR 2015-0067020A
(Patent Document 6) KR 2014-0137099A
(Patent Document 7) KR 2014-0088748A
(Patent Document 8) KR 2014-0070975A
(Patent Document 9) KR 2013-0139585A

DISCLOSURE

Technical Problem

The present invention has been made to solve the above problems.

Specifically, the present invention has been made in consideration of the fact that it is necessary for the warm ball to be mounted to the bracket and rotated to provide a massaging feeling, and also to provide a user with a sense of warmth at the same time, and accordingly, the present invention provides a heating assembly for a massage chair, which is capable of simultaneously providing a massaging feeling and a sense of warmth, while solving various problems described above.

In other words, it is an object of the present invention to provide a heating assembly which is capable of solving the problem of excessive heat generation of the bracket and preventing noise problems at the same time, which has a simpler structure of the warm ball, and which provides the sense of warmth accurately to a specific region as desired by a user.

Technical Solution

According to an aspect of the present invention, a heating assembly may include: a first bracket; a plurality of massage balls rotatably mounted to the first bracket; a massage assembly to which the first bracket is fixed, and which is capable of at least one of up-and-down and left-and-right motions; a second bracket mounted to the massage assembly or the first bracket; a support part inserted at one end thereof into the second bracket; a heating element mounted to the support part; and an airbag fixed to the support part so as to be opposite to the heating element, wherein the heating assembly is mounted inside a backrest of a massage chair.

In addition, the heating element may be linearly reciprocated between a first direction toward the backrest of the massage chair and a second direction opposite to the first direction, by adjustment of an amount of air of the airbag.

In addition, the second bracket may include a guide groove formed therein for restricting a movement of the heating element to a movement in either of the first direction or the second direction, and the support part may include a mounting protrusion to be inserted into the guide groove.

In addition, the heating assembly may perform at least one of up-and-down and left-and-right motions in a state in which the airbag is filled with air.

Further, the amount of air of the airbag may be adjusted in multiple stages.

Further, when a stretching mode is applied to the massage chair, the air may be filled into the airbag.

Further, when the heating element is heated, the air may be filled into the airbag.

Further, the heating element may be positioned adjacent to the plurality of massage balls, and the heating element may be positioned so as to be opposite to the plurality of massage balls with respect to the first bracket.

In addition, the heating element may include a heating wire provided therein.

In addition, the first bracket may include a mounting groove formed therein, and the second bracket may be mounted in the mounting groove.

Further, according to an aspect of the present invention, there is provided a heating assembly including: a bracket; a plurality of massage balls rotatably mounted to the bracket; a massage assembly to which the bracket is fixed, and which is capable of at least one of up-and-down and left-and-right motions; a heating element mounted to the massage assembly or the bracket and positioned adjacent to the plurality of massage balls; and an airbag fixed to the bracket at one end, wherein the airbag is positioned adjacent to the plurality of massage balls, and the heating assembly is mounted inside a backrest of a massage chair.

Further, the heating assembly may be reciprocated in a direction toward the backrest of the massage chair by adjustment of an amount of air of the airbag.

Further, according to another aspect of the present invention, there is provided a massage chair including the heating assembly described above, which may include: a seat; the backrest rotatably fixed to one side of the seat; a leg fasten part rotatably fixed to the other side of the seat; a support frame for fixing the seat; the heating assembly mounted into the backrest and capable of at least one of up-and-down and left-and-right motions by the massage assembly; and an operation unit capable of adjusting a rotation of the backrest, a rotation of the leg fasten part, and the up-and-down motion or the left-and-right motion of the heating assembly, and adjusting a heat generation of the heating element.

In addition, the operation unit may cause the heating element of the heating assembly to be reciprocated between a first direction toward the backrest and a second direction opposite to the first direction, by adjusting the amount of air of the airbag.

Further, the operation unit may cause the massage balls and the heating element of the heating assembly in a direction toward the backrest by adjusting the amount of air of the airbag.

Advantageous Effects

Unlike the traditional paradigm that the massaging feeling and the sense of warmth through self-heating of the massage ball are simultaneously provided to the user, the present invention separately adopts a massage ball that performs only a massage function, and a heating element that performs both a massage function and a heating function.

In particular, the heating element is made of a material having a higher heat transfer rate than the heat transfer rate of the bracket such that it is possible to prevent the phenomenon such as excessive heat up of the bracket, deteriorating durability of the bracket, or the like.

A heating element having a separate structure is attached adjacent to the massage ball and only the heating element is driven through an airbag, so that the structure of the massage ball and the heating element can be simplified, and depending on needs, the heating element can be provided adjacent to the conventional massage ball.

With this configuration, the material of the massage ball can be freely selected from those materials that can provide an optimum massaging feeling without generating noise, and accordingly, a massaging feeling superior to that of a related massage chair can be provided.

In addition, since the heating element can perform the heating function as well as the massage function at the same time, the sense of warmth and the massaging feeling can be provided to a user by using the heating element in a specific region as desired by the user, thereby meeting the user's needs accurately.

Further, since only the heating element can be driven as necessary, it is possible to prevent unnecessary power loss for driving the massage ball.

Unlike the traditional paradigm that it is necessary for the massage balls to heat up by themselves to provide the massaging feeling and the sense of warmth to the user at the same time, the present invention separately adopts a massage ball for performing the massage function and a heating element for performing a heating function.

This is based on the discovery that there is a somewhat thick exterior material (such as a leather sheet) placed between the heating assembly mounted into the backrest of the massage chair and the back or shoulder of the user, and that it is not absolutely necessary for the massage ball to heat up by itself, because, as long as the adjacent area is heated and the massage balls are moved up and down or left and right, the user will be able to feel both the massaging feeling and sense of warmth at the same time.

A heating element of a heating assembly according to a second embodiment of the present invention is made of a material having a higher heat transfer rate than the heat transfer rate of the bracket, so that it is possible to prevent the phenomenon such as excessive heat up of the bracket, deteriorating durability of the bracket, or the like.

Further, since the heating element is positioned adjacent to the massage ball, the user can simultaneously feel the massaging feeling as well as the sense of warmth as if the massage ball is heated up.

Further, since the airbag is positioned adjacent to the massage ball, it is possible to provide the effect of moxibustion and acupressure treatment.

With this configuration, the material of the massage ball can be freely selected from those materials that can give an optimum massaging feeling without generating noise, and accordingly, a massaging feeling superior to that of the related massage chair can be provided.

DESCRIPTION OF DRAWINGS

FIG. 8A and FIG. 8B are views showing a movement of the heating assembly according to expansion FIG. 8A and contraction FIG. 8B of the airbag according to the first embodiment of the present invention.

BEST MODE FOR INVENTION

Figure 1:
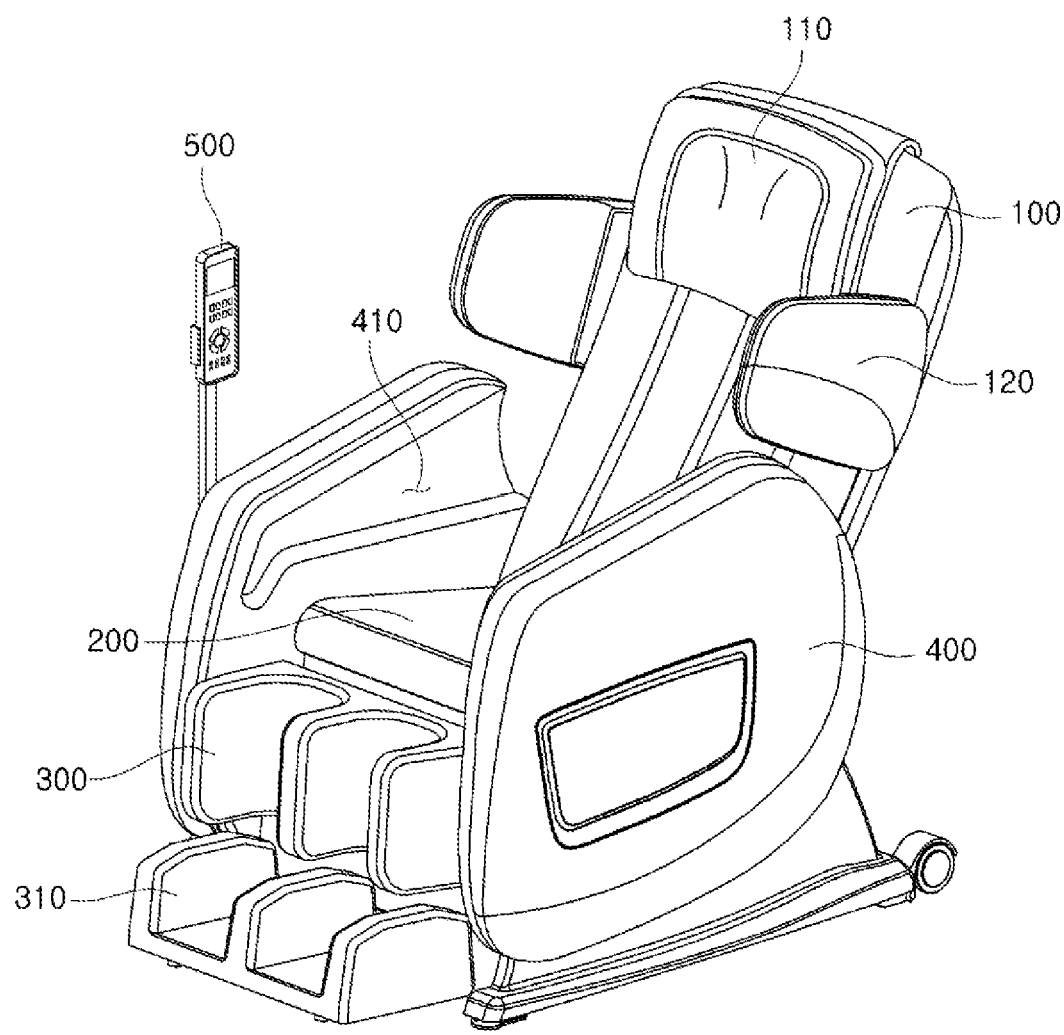
FIG. 1 is a perspective view showing a massage chair provided with a heating assembly according to a first embodiment of the present invention.

Hereinafter, the present invention will be described in detail with reference to the accompanying drawings.

In the drawings, when it is assumed that a user is seated on a massage chair, it is explained that an "upper side" refers to a side above the user, a "lower side" refers to a side under the user, a "front side" refers to a side in front where the user is facing, and a "rear side" refers to a side opposite the side where the user is facing, which is the direction where the back of the user is facing.

A backrest 100, a leg fasten part 300 and a foot fasten part 310, which will be described below, are each capable of moving in a rotary motion or moving in upward and downward directions, and a separate actuator (not shown) is provided for this purpose. Since this is a known technique, the principles of the operation thereof will not be described in detail.

In addition, selection and change of a mode according to an operation unit 500 (to be described below), and the corresponding operation of a massage chair are performed when a signal is applied to the operation unit 500 and the corresponding signal is transmitted to a controller (not shown). Since this is also a known technique, detailed description of the principles of the operation thereof be omitted.

Description of Massage Chair

A massage chair including a heating assembly 600 according to a first embodiment of the present invention and including a heating assembly 700 according to a second embodiment of the present invention will be described with reference to FIGS. 1 and 2.

The massage chair includes a backrest 100, a seat 200, a leg fasten part 300, a support frame 400, and an operation unit 500, and includes the heating assembly 600 according to the first embodiment of the present invention and the heating assembly 700 according to the second embodiment of the present invention.

The backrest 100 is configured to support the user's back and may be adjusted to a predetermined angle relative to the support frame 400 and the seat 200 which are stationary in position.

The heating assembly 600, which is movable, is mounted at the center of the backrest 100. The heating assembly 600 includes a plurality of massage balls 620, is heatable, and is movable up and down or left and right.

During a massage operation, the heating assembly 600 is moved along a predetermined trajectory, while a plurality of massage balls 620 press the back or shoulders of the user to provide a massaging feeling. This will be described below. A pair of back airbags 109 are mounted to both left and right sides of the backrest 100.

A head rest 110 to be in contact with the head of the user is positioned on an upper portion of the backrest 100.

A pair of shoulder fasten parts 120 are attached to both left and right sides of the head rest 110 of the backrest 100 and a shoulder airbag 129 is mounted to the shoulder fasten parts 120, respectively.

The pressure, or the amount of the air to be supplied to various airbags 109, 129, 209, 309, 319, 419 to be described below, including the airbag 109 and the shoulder airbag 129 may be adjusted.

Each of the airbags 109, 129, 209, 309, 319, and 419 needs only the level of pressure or amount of air that fastens the user's body without strongly pressing on a human body. Hereinafter, the air filled for this purpose is referred to as "air for fastening".

In addition, each of the airbags 109, 129, 209, 309, 319 and 419 needs a pressure or amount of air that is greater than the fastening air so as to perform the massage operation. Hereinafter, the air filled for this purpose is referred to as "air for massaging".

The seat 200 is a portion to be in contact with the hips and the upper thighs of the user, and is generally fixed to the support frame 400. The seat 200 is preferably made of a material that can provide a cushion feeling.

Pelvis airbags 209 are positioned on both sides of the seat 200, inwardly toward the user from where the seat 200 and the support frame 400 are joined with each other.

Each of the pelvis airbags 209 may include a pair of upper and lower airbags. In this case, the upper pelvis airbag 209 may be referred to as a waist airbag as it 209 may also press the waist.

Figure 2:
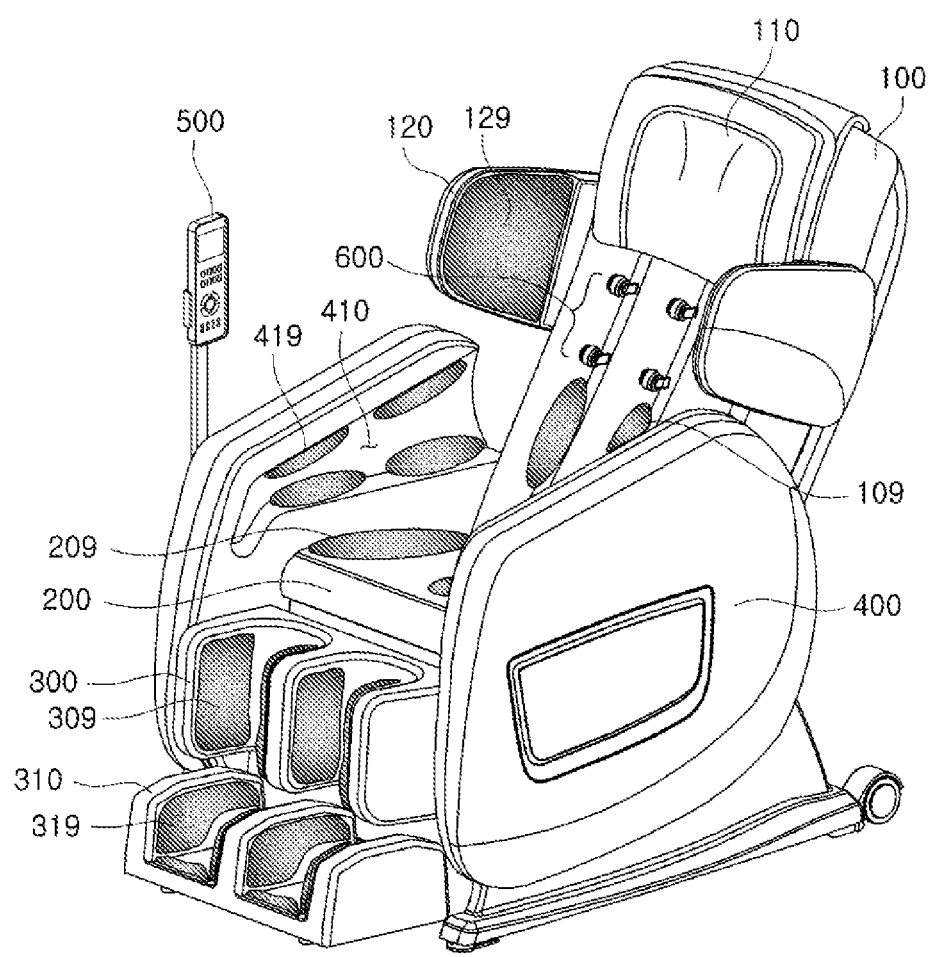
FIG. 2 is a perspective view showing an airbag of the massage chair of FIG. 1.
Figure 3:
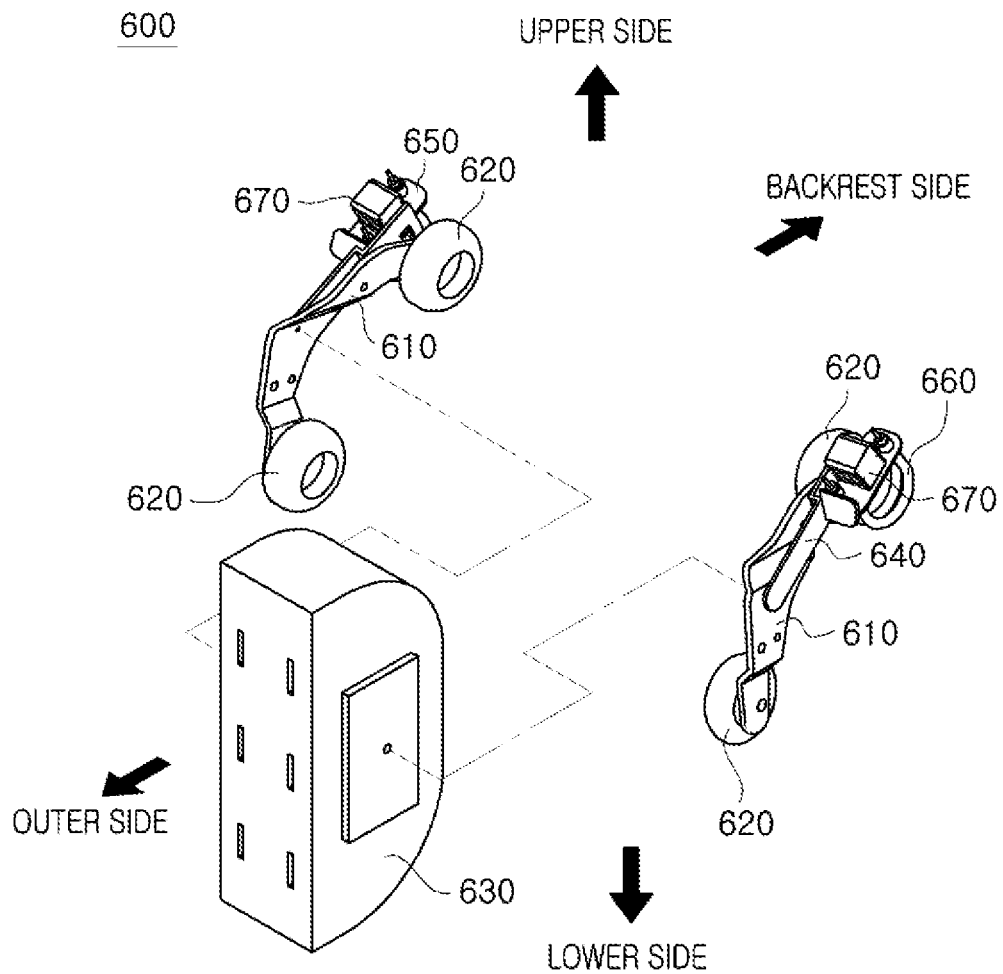
FIG. 3 is an exploded perspective view of the heating assembly according to the first embodiment of the present invention.

The leg fasten part 300 is configured to fasten the user's legs, and as shown in FIG. 2, is provided with a pair of grooves to receive the user's calves therein. The leg fasten part 300 is adjustable to a predetermined angle relative to the support frame 400 and the seat 200 which are stationary.

A leg airbag 309 is positioned in the groove of the leg fasten part 300.

Referring to FIG. 2, in the illustrated embodiment, there may be provided pairs of right and left airbags at upper and lower positions, respectively, such that one leg airbag 309 includes a total of four airbags. Alternatively, one leg airbag 309 may each include a pair of left and right airbags.

The foot fasten part 310 is configured to fasten the foot of the user during the massage operation, and is provided with a groove for receiving the user's foot inserted therein.

In the illustrated embodiment, the foot fasten part 310 is integrally formed with the leg fasten part 300. Alternatively, the foot fasten part 310 may be moved up and down relative to the leg fasten part 300, and may be appropriately adjusted according to the user's body size (such as the leg or calf length).

A foot airbag 319 is located in the groove of the foot fasten part 310.

Referring to FIG. 2, in the illustrated embodiment, there may be provided pairs of right and left airbags at upper and lower positions, respectively, such that the foot airbag 319 includes a total of four airbags. Alternatively, one foot airbag 319 may each include a pair of left and right airbags.

The support frame 400 is positioned on the left and right sides of the seat 200 and securely holds the massage chair as a whole even during operation of the backrest 100 and the leg fasten part 300 and during operation of the foot fasten part 310. To this end, a bracket capable of fixing the massage chair on the floor may be positioned at a lower end of the support frame 400.

An arm fasten part 410 is positioned on an upper end of the support frame 400.

The arm fasten part 410 is configured to fasten the arm of the user during the massage operation, and is provided with a groove (see FIG. 1) for allowing a user's foot to be inserted therein.

An arm airbag 419 is positioned in the groove of the arm fasten part 410.

In the illustrated embodiment, there are pairs of upper and lower airbags on left and right sides, respectively, such that one arm airbag 419 includes a total of four airbags. Alternatively, one arm airbag 419 may each include a pair of upper and lower airbags.

The operation unit 500 allows a user to operate the massage chair, and may include a button or a touch panel.

In the illustrated embodiment, the operation unit 500 is provided on the right side of the massage chair, thus allowing operating with a right hand. Alternatively, the operation unit 500 may be provided on the left side, thus allowing operating with a left hand.

It is preferable that the manipulation unit 500 and the massage chair are connected to each other by a material that is hard, but that is changeable in shape to some extent, and may be provided with a cable therein for connecting the operation unit 500 and a controller (not shown) inside the massage chair.

The user may select various modes through the operation unit 500 to apply a signal to the controller (not shown). Accordingly, the operation unit 500 transmits the signal corresponding to the mode to the controller (not shown).

The signal received by the controller may actuate an actuator (not shown) to operate the backrest 100, the leg fasten part 300 and the foot fasten part 310, thereby changing the respective angles or controlling the operations of the various air bags 109, 129, 209, 309, 319, and 419 and the heating assembly 600.

Description of Heating Assembly According to First Embodiment

One of the distinguishing features of the heat generating assembly 600 according to the first embodiment of the present invention from the related art is that the heating element 660 is driven independently from the massage ball 620 so that the user is provided with a sense of warmth and a massaging feeling by the heating element 660 without the massage ball 620 being moved or heated.

In the massage chair according to the related art, in order to simultaneously provide the massaging feeling and the sense of warmth to the user, the massage ball contacting the user's back or shoulder need to be rotated and heated simultaneously, which was confirmed as the problem of the related art by the present inventors.

Thus, with the heating assembly 600 according to the first embodiment of the present invention, the massage ball 620 is not heated, but only rotated and moved up and down or left and right.

A second bracket 640 provided with the separate heating element 660 is mounted adjacent to the massage ball 620, and on the massage assembly 630 or the first bracket 610 to be driven independently of the massage ball 620.

As a result, the problems according to the related art described above is solved, while the user may feel the massaging feeling and the sense of warmth like the related art by the heating element 660 alone.

Hereinafter, the heating assembly 600 according to the first embodiment will be described more specifically with reference to FIGS. 2 to 6.

The heating assembly 600 is mounted to the backrest 100 of the massage chair and includes the first bracket 610, a plurality of massage balls 620, the massage assembly 630, the second bracket 640, and the support part 650.

The plurality of massage balls 620 are rotatably mounted to the first bracket 610, and also the first bracket 610 is fixed to the massage assembly 630 and moved together with the massage assembly 630 when the massage assembly 630 is moved up and down or left and right.

Accordingly, the massage ball 620 mounted to the first bracket 610 is also moved together. In addition, the second bracket 640, which will be described below, may be mounted to the mounting groove 612 of the first bracket 610.

The first bracket 610 may be provided with a separate electric wire (not shown) to transfer the power supplied from a power supply (not shown) to the heating element 660.

According to the related technology, it is necessary to supply the power to the rotating massage ball, and this makes the structure complicated. According to the present invention, however, since the power is supplied to the non-rotating heating element 660, the structure is simplified.

The massage ball 620 is configured to provide the massaging feeling to the user. The massage ball 620 is not heated separately, and the massage ball 620 is moved up and down or left and right together with the massage assembly 630 as the massage assembly 630 is moved up and down or left and right.

At this time, the massage ball 620 can be naturally rotated upon contacting the back or shoulder of the user in up-and-down or left-and-right motion, and this rotation of the massage ball 620 provides the massaging feeling to the user.

Any material may be used for the massage ball 620 as long as the material provides an optimal massaging feeling to the user and minimizes noise during the rotation. In the first embodiment, since the separate heating element 660 is provided, it is not necessary to take the heat transfer rate of the massage ball 620 into consideration.

Therefore, any material that suits the purpose of the massage chair may be selected from among elastic rubbers or synthetic resin series.

The massage assembly 630 provides the power for the heating assembly 600 to perform at least one of up-and-down and left-and-right motions. The massage assembly 630 is mounted with an actuator (not shown) for supplying the power to the heating assembly 600.

In addition, the massage assembly 630 provides the power supplied from the power supply (not shown) to the heating element 660 and the airbag 670 to be described below through a separate electric wire (not shown) provided in the first bracket 610, the second bracket 640 and the like.

The first bracket 610 is mounted to the massage assembly 630. In the illustrated embodiment, the massage assembly 630 and the first bracket 610 are coupled by nut through the mounting groove 612.

Figure 4:
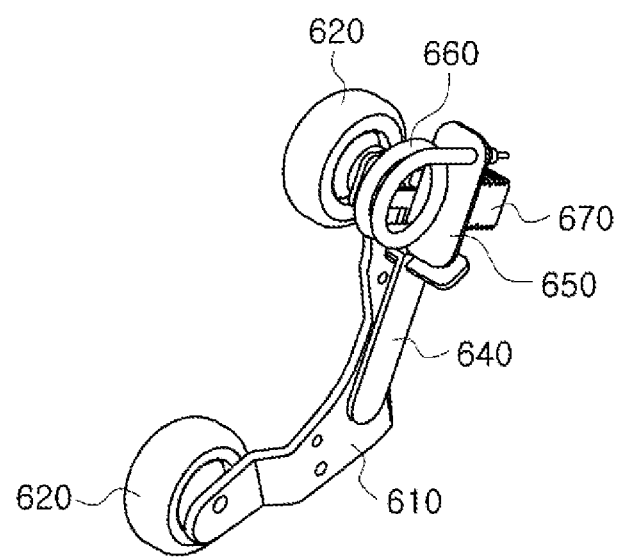
FIG. 4 is a perspective view showing a part of the heating assembly of FIG. 3.
Figures 5A, 5B:
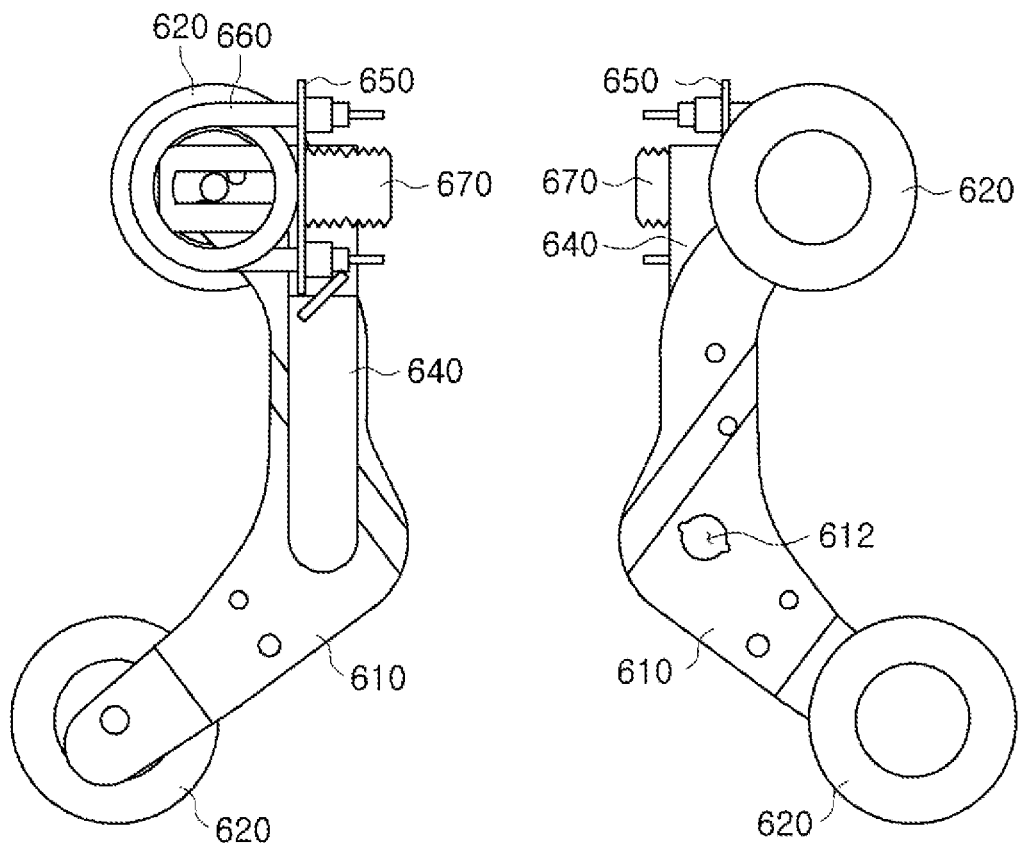
FIG. 5A is a right side view and FIG. 5B is a left side view of a part of the heating assembly of FIG. 4.

Referring to FIGS. 4 and 5, the support part 650 is coupled to the second bracket 640 and the second bracket 640 is mounted to the first bracket 610 through the mounting groove 612 of the first bracket 610. The heating element 660 and the airbag 670, which will be described below, are mounted to the support part 650. Alternatively, the second bracket 640 may be mounted to the massage assembly 630.

Figure 6:
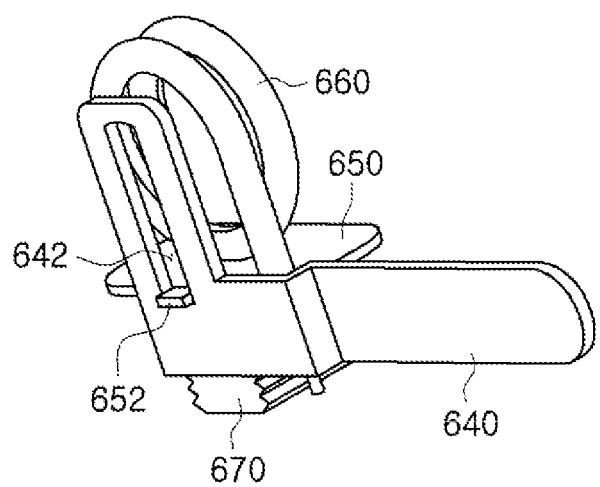
FIG. 6 is an enlarged view of a part of the heating assembly of FIG. 4.

Referring to FIG. 6, a guide groove 642 is formed in the second bracket 640, and a mounting protrusion 652 of the support part 650 to be described below is inserted into the guide groove 642.

The movement of the heating element 660 including the support part 650 is limited to the linear movement in either of a first direction toward the backrest 100 of the massage chair or a second direction opposite to the first direction.

In the illustrated embodiment, the heating element 660 is mounted to the support part 650 in a penetrating manner. The heating element 660 is not limited thereto and may be mounted to the support part 650 in various ways.

In addition, one end of the airbag 670 is fixed to the support part 650 so as to be opposite to the heating element 660. Therefore, as described below, the support part 650 and the heating element 660 are integrally moved by the contraction and expansion of the airbag 670.

A mounting protrusion 652 is formed on one side of the support part 650. The mounting protrusion 652 is inserted into the guide groove 642 of the second bracket 640. By the guide groove 642, the movement of the support part 650 and the heating element 660 is restricted to the movement in either of the first direction or the second direction.

The second bracket 640 and the support part 650 preferably have a thermal conductivity lower than that of the heating element 660 to be described below.

When the heating element 660 is formed of a material having a higher thermal conductivity than the thermal conductivity of the second bracket 640 and the support part 650 which are made of metal, transfer of the heat to the support part 650 and the second bracket 640 during the heat generation of the heating element 660 can be prevented.

In addition, it is preferable that the heating element 660 and the second bracket 640 are spaced apart from each other by a predetermined distance in order to further prevent the transfer of the heat generated in the heating element 660, which will be described below, to the second bracket 640.

The heating assembly 600 according to the first embodiment of the present invention also includes the heating element 660 and the airbag 670.

The heating element 660 provides the sense of warmth to the user through heat generation, and at the same time, provides the massaging feeling to the user by pressing. Therefore, the user may be provided with the same effect as the moxibustion pressure on the desired portion. To this end, in the illustrated embodiment, the air may be filled into the airbag 670 when the heating element 660 is heated.

Referring to FIGS. 4 to 6, the heating element 660 is mounted to the second bracket 640, and is mounted to the support part 650 so as to be opposite to the heating element 660, while being integrated with the airbag 670 that has one end fixed to the support part 650.

The heating element 660 is heated by the power supplied from a separate power supply (not shown) through electric wires (not shown) and the like that are provided in the massage assembly 630, the first bracket 610, and the second bracket 640. In the illustrated embodiment, the heating element 660 is provided with a heating wire for heating. Alternatively, the heating element 660 may have a structure employing a sheath heater.

The heating element 660 does not rotate. Therefore, unlike the heating structure according to the related art in which the rotating massage ball is heated, the power may be transferred with a simple structure.

The heating element 660 has a shape of a coil of a wound heating wire. Alternatively, the heating element 660 may be formed in any shape as long as it is a structure capable of heating with the transferred power. This is possible because the heating element 660 does not need to rotate.

The heating element 660 is fixed to the support part 650 such that the heating element 660, integrally with the support part 650, is coupled to the second bracket 640. In the illustrated embodiment, the second bracket 640 coupled with the heating element 660 is mounted to the first bracket 610 to be adjacent to the massage ball 620.

Thus, the heating element 660 is positioned adjacent to the massage ball 620. Alternatively, the second bracket 640 may be mounted to the massage assembly 630.

Since the heating element 660 is driven independently of the massage ball 620, it is preferable that the heating element 660 is positioned so as to be opposite to the massage ball 620 with respect to the first bracket 610 so that the heating element 660 and the massage ball 620 do not interfere with each other. Referring to FIGS. 4 and 5, the heating element 660 may be positioned to be opposite to the massage ball 620 such that the first bracket 610 and the second bracket 640 are disposed between the heating element 660 and the massage ball 620 between the first bracket 610 and the second bracket 640.

The heating element 660 is driven independently of the massage ball 620, and the heating element 660 may not only provide the user with the sense of warmth through heating, but also provide the massaging feeling to the user through the pressing by the heating element 660 itself.

The heating element 660 may be moved in either of the first direction or the second direction by the airbag 670 to be described below to provide the user with the sense of warmth and the massaging feeling.

Figure 7:
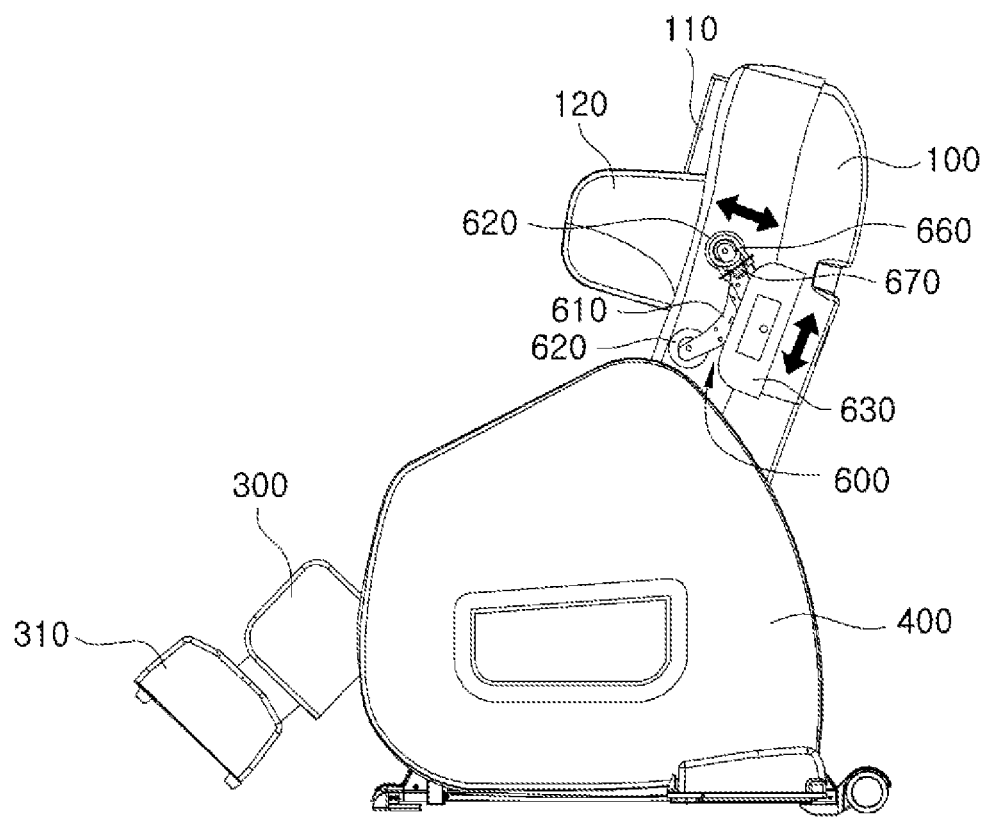
FIG. 7 is a side view of a massage chair including the heating assembly of FIG. 3.

Referring to FIG. 7, the airbag 670 has one end fixed to the support part 650 so as to be opposite to the heating element 660, and the amount of air in the airbag 670 is adjusted to cause the heating element 660 to be reciprocated in the first direction toward the backrest 100 of the massage chair and the second direction opposite to the first direction.

More specifically, referring to FIG. 8A, when the airbag 670 is expanded, the support part 650 is pushed up so that the heating element 660 mounted to the support part 650 is also moved in the first direction.

At this time, the mounting protrusion 652 of the support part 650 is inserted into the guide groove 642 formed in the second bracket 640. Therefore, the movement of the heating element 660 is restricted by the guide groove 642 to the linear movement toward the first direction, and the moving distance of the heating element 660 is also limited by the length of the guide groove 642. Referring to FIG. 8(a), when the airbag 670 is expanded, the heating element 660 is moved to a position where the heating element 660 is protruded farther toward the backrest compared to the massage ball.

Referring to FIG. 8B, when the airbag 670 is contracted, the support part 650 is pulled down so that the heating element 660 mounted to the support part 650 is also moved in the second direction.

At this time, the mounting protrusion 652 of the support part 650 is inserted into the guide groove 642 formed in the second bracket 640.

Therefore, the movement of the heating element 660 is restricted by the guide groove 642 to the linear movement to the second direction, and the moving distance of the heating element 660 is also limited by the length of the guide groove 642.

At this time, the amount of air in the airbag 670 may be adjusted in multiple stages and the heating assembly 600 according to the first embodiment performs at least one of up-and-down and left-and-right motions while the air is being filled into the airbag 670.

That is, in the state that the air is filled into the airbag 670 and the heating element 660 is moved in the first direction, the heating assembly 600 performs at least one of up-and-down and left-and-right motions.

Accordingly, the user may be provided with the sense of warmth and the massaging feeling at a desired region by the heating element 660. In addition, by moving the heating assembly 600, the effect of moxibustion pressure may be obtained at various desired regions.

At this time, the airbag 670 does not influence the movement of the massage ball 620, but drives only the heating element 660.

In another embodiment, the airbag 670 may be filled with air inside when the stretching mode is applied to the massage chair, thereby providing the user with the pressure for stretching. In this case as well, it is needless to say that the heating element 660 is driven to provide the user with the sense of warmth and the massaging feeling at the same time.

Description of Heating Assembly 700 According to Second Embodiment

One of the distinguishing features of the heating assembly 700 according to the second embodiment from the related art is that the massage ball 710 provides the user with a sense of warmth without having to generate heat.

In the massage chair according to the related art, in order to simultaneously provide the massaging feeling and the sense of warmth to the user, the massage ball contacting the user's back or shoulder need to be rotated and heated simultaneously, which was confirmed as the problem of the related art by the present inventors.

That is, in the heating assembly 700 according to the second embodiment, the massage ball 710, which contacts the back or shoulder of the user and provides a massaging feeling, does not generate heat, but is only rotated and moved up and down or left and right, while there is a separate heating element 720 adjacent to the massaging ball 710, which is mounted to the massage assembly 750 or the bracket 730, so that the problems according to the related art described above are solved, and the user may still feel the massaging feeling and the sense of warmth like the related art.

Figure 9:
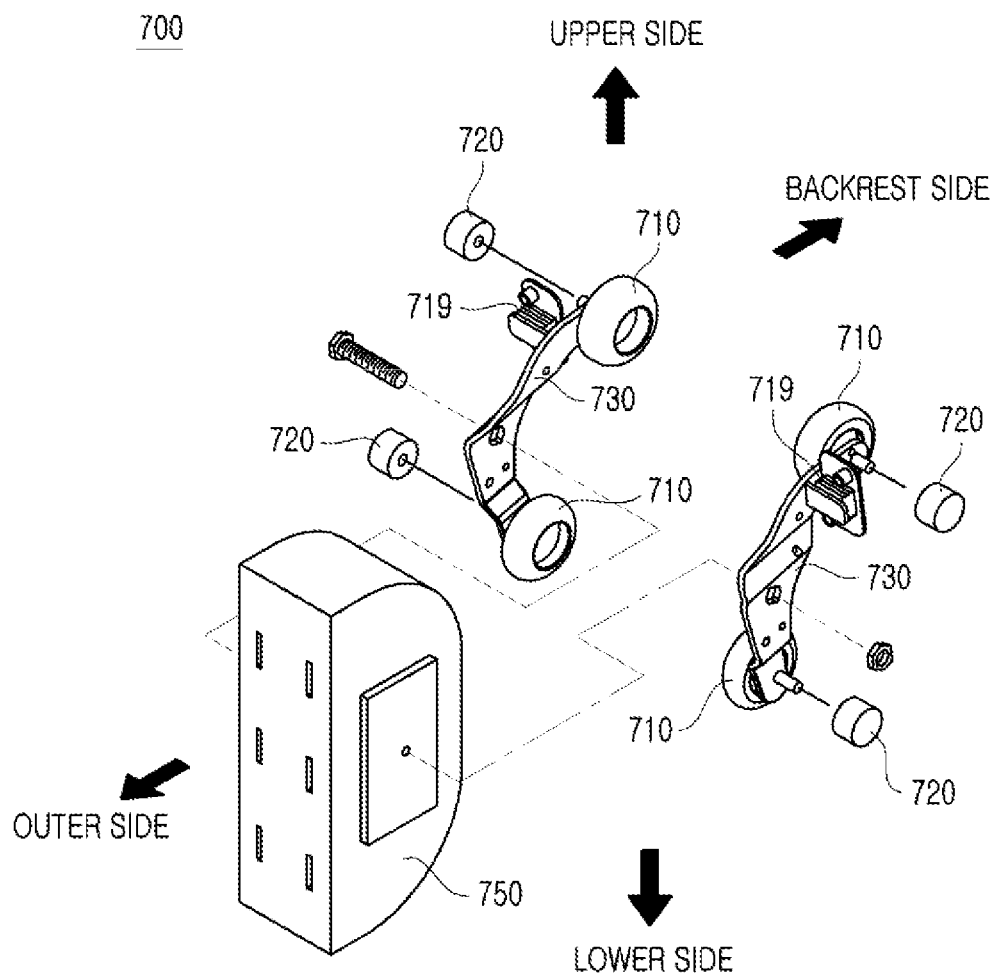
FIG. 9 is an exploded perspective view of a heating assembly according to a second embodiment of the present invention.
Figure 10:
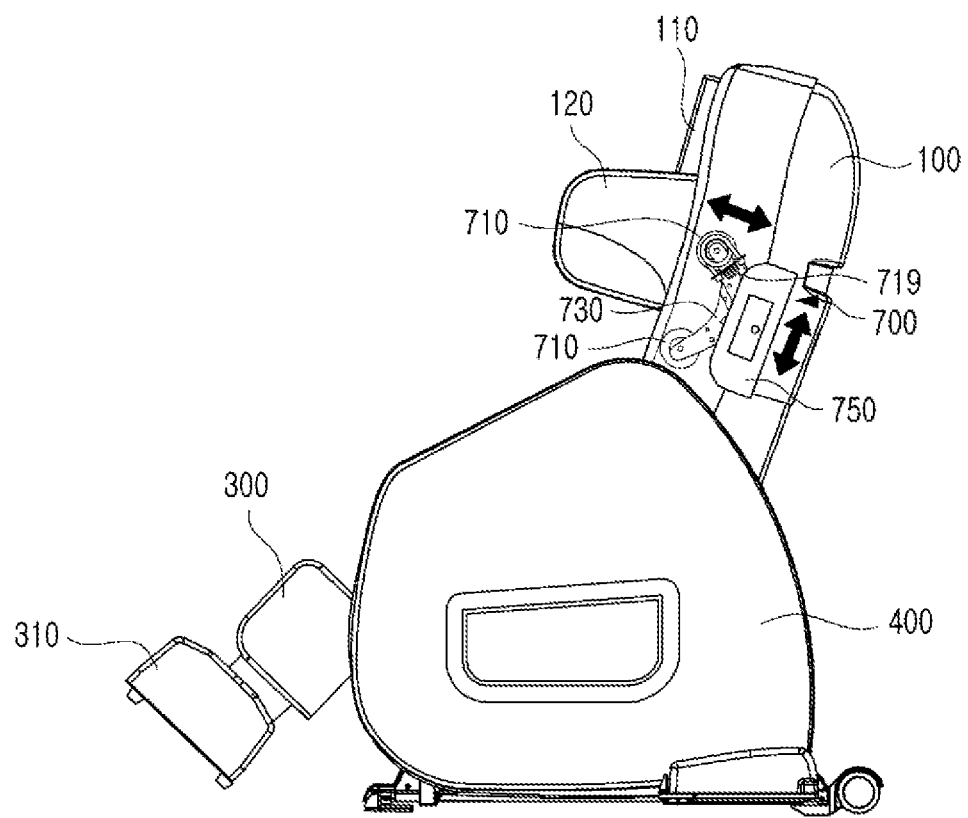
FIG. 10 is a side view of a massage chair including the heating assembly of FIG. 9.

Hereinafter, the heating assembly 700 according to the second embodiment will be described more specifically with reference to FIGS. 9 and 10.

The heating assembly 700 according to the second embodiment may be mounted at the same position as the heating assembly 600 according to the first embodiment (see FIG. 2).

The heating assembly 700 is mounted to the backrest 100 in the massage chair and includes a plurality of massage balls 710 that are rotatable, an airbag 719 and a heating element 720 positioned adjacent to the massage ball 710, a bracket 730 for fixing the massage ball 710, the airbag 719 and the heating element 720, and a massager 750 which is fixed to support the bracket 730 and supplies power such that the entire heat generating assembly 700 may perform at least one of up-and-down and left-and-right motions.

The massage ball 710 is not heated separately, and moved up and down or left and right together with the massage assembly 750 when the massage assembly 750 is moved up and down or left and right.

At this time, the massage ball 710 can be naturally rotated upon contacting the back or shoulder of the user in up-and-down or left-and-right motion, and this rotation of the massage ball 710 provides the massaging feeling to the user.

Any material may be used for the massage ball 710 as long as the material provides an optimal massaging feeling to the user and minimizes noise during the rotation.

In the related art, since the massage ball itself is heated, it is necessary to use a material resistant to heat or a material having a high heat transfer rate, and as a result, a material which is somewhat poor in terms of the massaging feeling is adopted, or noise is arisen during rotation.

According to the illustrated embodiment, since it is not necessary to consider the heat transfer rate, any material that suits the purpose of the massage chair may be selected from among elastic rubbers or synthetic resin series.

One end of the airbag 719 is fixed to the bracket 730, and positioned adjacent to the plurality of massage balls 710. The amount of air inside of the airbag 719 is adjusted, so that the airbag 719 causes the massage ball 710 to reciprocate in the direction toward the backrest 100 of the massage chair.

In addition, the amount of air in the airbag 719 may be adjusted in multiple stages, and the heating assembly according to the second embodiment performs at least one of up-and-down and left-and-right motions while having the air filled in the airbag 670.

In this case, the massage ball 710 may provide the user with the massaging feeling by separate pressure, and the massage ball 710 and the heating assembly may also provide the user with the same effect as the moxibustion pressure by giving the sense of warmth and pressure feeling at once. To this end, in one embodiment, the air may be filled into the airbag 719 when the heating element 720 to be described below is heated.

In another embodiment, the airbag 719 may be filled with air when a stretching mode is applied to the massage chair, thereby providing the user with the pressure for stretching.

The heating element 720 is mounted at a predetermined distance from the bracket 730 or the massage assembly 750, and in an embodiment, the heating element 720 is mounted to the bracket 730.

The heating element 720 mounted to the bracket 730 is heated by the power supplied from a separate power supply (not shown) through electric wires (not shown) and the like provided in the massage assembly 750 and the second bracket 730. Any structure may be used for heating. For example, a specific structure for heating may adopt a heat wire or a sheath heater.

The heating element 720 does not rotate. Therefore, unlike the heating structure according to the related art in which the rotating massage ball is heated, the power may be transferred with a simple structure.

The number of heating elements 720 is not limited, but the number of heating elements 720 is the same as the number of massage balls 710. When the numbers are the same as each other, as described below, when the user is provided with the massaging feeling from any massage ball 710, the user is also provided with the sense of warmth from the heating element 720 adjacent to that massage ball 710. In the drawing, the massage ball 710 and the heating element 720 are shown in total of six including three on the left side and three on the right side, but it goes without saying that the number may be less or more than this.

The heating element 720 should be positioned adjacent to the massage ball 710. This is because the user has to be provided with not only the massaging feeling, but also the sense of warmth in the vicinity of the rotating massage ball 710, in order to have increased massage effect from feeling both the massaging feeling and the sense of warmth at the same time.

In fact, when the heating element 720 positioned adjacent to the massage ball 710 is heated, since there is an exterior material (not shown) such as a leather sheet or cushion between the heating assembly 700 and the back or shoulder of the user, the user feels the sense of warmth as if the massage ball 710 is heated.

To this purpose, the heating element 720 is positioned so as to be opposite to the massage ball 710 with respect to the bracket 730. That is, with respect to the bracket 730, the massage ball 710 is positioned inside and the heating element 720 is positioned outside.

Furthermore, since the number of heating elements 720 is the same as the number of massage balls 710, the user feeling a particularly excellent massaging feeling from any massage ball 710 may simultaneously feel the sense of warmth from the heating element 720 located opposite to that massage ball.

The bracket 730 supports the massage ball 710 as well as the airbag 719 and the heating element 720 positioned adjacent to the massage ball 710 and is connected to the massage assembly 750 to move the massage ball 710 and the heating element 720 together when the massage assembly 750 is moved up and down or left and right.

It is preferable that the thermal conductivity of the bracket 730 is lower than the thermal conductivity of the heating element 720.

According to the second embodiment, unlike the related art, since the heating element 720 does not perform the massage function, the structure and material may be freely selected. Meanwhile, when the heating element 720 is formed of a material having a thermal conductivity higher than the thermal conductivity of the metal bracket 730, transfer of the heat to the bracket 730 can be prevented when the heat generating body 720 generates heat.

In addition, it is preferable that the heating element 720 and the bracket 730 are spaced apart from each other by a predetermined distance in order to further prevent the transfer of the heat generated from the heating element 720 to the bracket 730.

The bracket 730 may be provided with a separate electric wire (not shown) to transfer the power supplied from the power supply (not shown) to the heating element 720.

it is necessary to supply the power to the rotating massage ball, and this makes the structure complicated. According to the second embodiment, however, since the power is supplied to the non-rotating heating element 660, the structure is simplified.

The massage assembly 750 is provided with an actuator (not shown) that is supplied with power from a power supply (not shown) of the massage chair and performs at least one of the up-and-down or left-and-right motions of the heating assembly 700.

In addition, the massage assembly 750 provides the power supplied from the power supply (not shown) to the airbag 719 and the heating element 720 through a separate electric wire (not shown) provided in the bracket 730 or the like.

While the present invention has been described with reference to exemplary embodiments thereof in order that those skilled in the art can readily understand and reproduce the invention, which is merely an example, it will be understood by those skilled in the art that various changes and modifications may be made without departing from the scope of the present invention. Accordingly, the scope of protection of the present invention should be determined by the claims.

DESCRIPTION OF REFERENCE NUMERALS

100: backrest
109: back airbag
110: head rest
120: shoulder fasten part
129: shoulder airbag
200: seat
209: pelvis airbag
300: leg fasten part
309: leg airbag
310: foot fasten part
319: foot airbag
400: support frame
410: arm fasten part
419: arm airbag
500: operation unit
600: heating assembly
610: first bracket
612: mounting groove
620: massage ball
630: massage assembly
640: second bracket
642: guide groove
650: support part
652: mounting protrusion
660: heating element
670: airbag
700: heating assembly
710: massage ball
719: airbag
720: heating element
730: bracket
750: massage assembly

The invention claimed is:
1. A heating assembly, comprising:
a massage assembly which is mounted inside a backrest of a massage chair, and which is capable of at least one of up-and-down and left-and-right motions;
a first bracket mounted to the massage assembly and moving with the massage assembly;
a plurality of massage balls rotatably mounted to the first bracket;
a second bracket mounted to the first bracket and having a guide groove formed therein;
a support part including a mounting protrusion to be inserted into the guide groove;

a heating element facing the massage ball with the first bracket and the second bracket interposed therebetween, mounted on one end of the support part to be spaced apart from the second bracket by a predetermined distance, and receiving power to generate heat; and an airbag mounted on the other end of the support part so as to face the heating element between the support part, wherein the mounting protrusion of the support part moves along the guide groove according to the amount of air injected into the airbag, and the heating element is movable in a first direction toward the backrest of the massage chair and in a second direction opposite to the first direction.

2. The heating assembly of claim 1, wherein the amount of air of the airbag is adjusted in multiple stages.

3. The heating assembly of claim 1, wherein, when a stretching mode is applied to the massage chair, the air is filled into the airbag.

4. The heating assembly of claim 1, wherein, when the heating element is heated, the air is filled into the airbag.

5. The heating assembly of claim 1, wherein the heating element includes a heating wire provided therein.

6. The heating assembly of claim 1, wherein the first bracket includes a mounting groove formed therein, and the second bracket is mounted in the mounting groove.

7. A massage chair comprising the heating assembly of claim 1, comprising:
 a seat;
 the backrest rotatably fixed to one side of the seat;
 a leg fasten part rotatably fixed to the other side of the seat;
 a support frame for fixing the seat;
 the heating assembly mounted into the backrest and capable of at least one of up-and-down and left-and-right motions with the massage assembly; and
 an operation unit capable of adjusting a rotation of the backrest, a rotation of the leg fasten part, and the up-and-down motion or the left-and-right motion of the massage assembly, and adjusting a heat generation of the heating element.

8. The massage chair of claim 7, wherein the operation unit causes the heating element of the heating assembly to be reciprocated between a first direction toward the backrest and a second direction opposite to the first direction, by adjusting an amount of air of the airbag.

9. The massage chair of claim 7, wherein the operation unit causes the heating assembly to move in a first direction toward the backrest and a second direction opposite to the first direction by adjusting an amount of air of the airbag.

* * * * *